(12) United States Patent
Inman et al.

(10) Patent No.: US 8,180,462 B2
(45) Date of Patent: May 15, 2012

(54) HEAT DISSIPATION FOR A LEAD ASSEMBLY

(75) Inventors: D. Michael Inman, Seabrook, TX (US); Jason D. Begnaud, Houston, TX (US)

(73) Assignee: Cyberonics, Inc., Houston, TX (US)

( * ) Notice: Subject to any disclaimer, the term of this patent is extended or adjusted under 35 U.S.C. 154(b) by 492 days.

(21) Appl. No.: 11/405,939

(22) Filed: Apr. 18, 2006

(65) Prior Publication Data
US 2007/0244535 A1 Oct. 18, 2007

(51) Int. Cl.
*A61N 1/00* (2006.01)
(52) U.S. Cl. ............................ 607/117; 607/45; 607/116
(58) Field of Classification Search .................. 607/45, 607/116–117
See application file for complete search history.

(56) References Cited

U.S. PATENT DOCUMENTS

| | | | |
|---|---|---|---|
| 3,421,511 A | 1/1969 | Schwartz et al. |
| 3,760,812 A | 9/1973 | Timm et al. |
| 3,796,221 A | 3/1974 | Hagfors |
| 4,291,699 A | 9/1981 | Geddes et al. |
| 4,305,402 A | 12/1981 | Katims |
| 4,384,926 A | 5/1983 | Wagner |
| 4,407,303 A | 10/1983 | Akerstrom |
| 4,458,696 A | 7/1984 | Larimore |
| 4,459,989 A | 7/1984 | Borkan |
| 4,573,481 A | 3/1986 | Bullara |
| 4,590,946 A | 5/1986 | Loeb |
| 4,592,359 A | 6/1986 | Galbraith |
| 4,606,349 A | 8/1986 | Livingston et al. |
| 4,608,985 A | 9/1986 | Crish et al. |
| 4,612,934 A | 9/1986 | Borkan |
| 4,628,942 A | 12/1986 | Sweeney et al. |
| 4,630,615 A | 12/1986 | Yomtov |
| 4,649,936 A | 3/1987 | Ungar et al. |
| 4,702,254 A | 10/1987 | Zabara |
| 4,793,353 A | 12/1988 | Borkan |
| 4,821,724 A | 4/1989 | Whigham et al. |
| 4,827,932 A | 5/1989 | Ideker et al. |

(Continued)

FOREIGN PATENT DOCUMENTS
WO 2004/069330 8/2004

OTHER PUBLICATIONS

J. Walter Woodbury and Dixon M. Woodbury, Vagal Stimulation Reduces the Severity of Maximal Electroshock Seizures in Intact Rates: Use of a Cuff Electrode for Stimulating and Recording, Department of Physiology, School of Medicine, University of Utah, Jan. 1991, pp. 94-107, vol. 14, Salt Lake City, Utah.

(Continued)

*Primary Examiner* — Nicole F Lavert
(74) *Attorney, Agent, or Firm* — Timothy L. Scott; Darrell N. Fuller; Jonathan D. Rowell

(57) ABSTRACT

A method, system, and apparatus are provided for using an electrode for delivering an electrical signal to a first tissue of a patient's body. An electrode system comprises a lead and an electrode coupled to the lead. The electrode includes a stimulation portion that couples to the first tissue to deliver an electrical signal to the first tissue. The electrode also includes a dissipation portion that does not interface with the first tissue. The dissipation portion is adapted to dissipate thermal energy from the electrode.

22 Claims, 12 Drawing Sheets

U.S. PATENT DOCUMENTS

| | | |
|---|---|---|
| 4,850,356 A | 7/1989 | Heath |
| 4,860,616 A | 8/1989 | Smith |
| 4,867,164 A | 9/1989 | Zabara |
| 4,870,341 A | 9/1989 | Pihl et al. |
| 4,899,750 A | 2/1990 | Ekwall |
| 4,903,700 A | 2/1990 | Whigham et al. |
| 4,920,979 A | 5/1990 | Bullara |
| 4,964,407 A | 10/1990 | Baker, Jr. et al. |
| 4,969,468 A | 11/1990 | Byers et al. |
| 4,979,511 A | 12/1990 | Terry, Jr. |
| 5,003,975 A | 4/1991 | Hafelfinger et al. |
| 5,025,807 A | 6/1991 | Zabara |
| 5,095,905 A | 3/1992 | Klepinski |
| 5,111,815 A | 5/1992 | Mower |
| 5,137,020 A | 8/1992 | Wayne et al. |
| 5,137,021 A | 8/1992 | Wayne et al. |
| 5,139,028 A | 8/1992 | Steinhaus et al. |
| 5,146,920 A | 9/1992 | Yuuchi et al. |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,201,808 A | 4/1993 | Steinhaus et al. |
| 5,201,865 A | 4/1993 | Kuehn |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,237,991 A | 8/1993 | Baker, Jr. et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,515 A | 7/1994 | Rutecki et al. |
| 5,335,657 A | 8/1994 | Terry, Jr. et al. |
| 5,351,394 A | 10/1994 | Weinberg |
| 5,411,528 A | 5/1995 | Miller et al. |
| 5,431,692 A | 7/1995 | Hansen et al. |
| 5,466,255 A | 11/1995 | Franchi |
| 5,501,702 A | 3/1996 | Plicchi et al. |
| 5,507,786 A | 4/1996 | Morgan et al. |
| 5,522,865 A | 6/1996 | Schulman et al. |
| 5,531,778 A | 7/1996 | Maschino et al. |
| 5,534,018 A | 7/1996 | Wahlstrand et al. |
| 5,540,730 A | 7/1996 | Terry, Jr. et al. |
| 5,540,734 A | 7/1996 | Zabara |
| 5,549,646 A | 8/1996 | Katz et al. |
| 5,571,150 A | 11/1996 | Wernicke et al. |
| 5,575,813 A | 11/1996 | Edell et al. |
| 5,620,474 A | 4/1997 | Koopman |
| 5,658,318 A | 8/1997 | Stroetmann et al. |
| 5,690,681 A | 11/1997 | Geddes et al. |
| 5,700,282 A | 12/1997 | Zabara |
| 5,707,400 A | 1/1998 | Terry, Jr. et al. |
| 5,713,936 A | 2/1998 | Staub et al. |
| 5,741,311 A | 4/1998 | Mc Venes et al. |
| 5,743,860 A | 4/1998 | Hively et al. |
| 5,755,742 A | 5/1998 | Schuelke et al. |
| 5,755,747 A | 5/1998 | Daly et al. |
| 5,759,199 A | 6/1998 | Snell et al. |
| 5,769,873 A | 6/1998 | Zadeh |
| 5,796,044 A * | 8/1998 | Cobian et al. ................. 174/103 |
| 5,814,088 A | 9/1998 | Paul et al. |
| 5,876,425 A | 3/1999 | Gord et al. |
| 5,891,179 A | 4/1999 | Er et al. |
| 5,897,577 A | 4/1999 | Cinbis et al. |
| 5,916,239 A | 6/1999 | Geddes et al. |
| 5,919,220 A | 7/1999 | Stieglitz et al. |
| 5,928,272 A | 7/1999 | Adkins et al. |
| 5,995,868 A | 11/1999 | Osorio et al. |
| 6,035,237 A | 3/2000 | Schulman et al. |
| 6,052,624 A | 4/2000 | Mann |
| 6,073,050 A | 6/2000 | Griffith |
| 6,104,956 A | 8/2000 | Naritoku et al. |
| 6,154,678 A | 11/2000 | Lauro |
| 6,171,239 B1 | 1/2001 | Humphrey |
| 6,181,969 B1 | 1/2001 | Gord |
| 6,208,902 B1 | 3/2001 | Boveja |
| 6,212,431 B1 | 4/2001 | Hahn et al. |
| 6,216,045 B1 | 4/2001 | Black et al. |
| 6,259,951 B1 | 7/2001 | Kuzma et al. |
| 6,269,270 B1 | 7/2001 | Boveja |
| 6,304,787 B1 | 10/2001 | Kuzma et al. |
| 6,317,633 B1 | 11/2001 | Jorgenson et al. |
| 6,339,725 B1 | 1/2002 | Naritoku et al. |
| 6,341,236 B1 | 1/2002 | Osorio et al. |
| 6,393,325 B1 | 5/2002 | Mann et al. |
| 6,400,988 B1 | 6/2002 | Gurewitsch |
| 6,418,348 B1 | 7/2002 | Witte |
| 6,445,951 B1 | 9/2002 | Mouchawar |
| 6,453,198 B1 | 9/2002 | Torgerson et al. |
| 6,456,481 B1 * | 9/2002 | Stevenson ..................... 361/302 |
| 6,473,653 B1 | 10/2002 | Schallhorn et al. |
| 6,477,417 B1 | 11/2002 | Levine |
| 6,490,486 B1 | 12/2002 | Bradley |
| 6,505,074 B2 | 1/2003 | Boveja et al. |
| 6,510,332 B1 | 1/2003 | Greenstein |
| 6,529,774 B1 | 3/2003 | Greene |
| 6,553,263 B1 | 4/2003 | Meadows et al. |
| 6,556,868 B2 | 4/2003 | Naritoku et al. |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,600,957 B2 | 7/2003 | Gadsby |
| 6,606,523 B1 | 8/2003 | Jenkins |
| 6,609,025 B2 | 8/2003 | Barrett et al. |
| 6,620,186 B2 | 9/2003 | Saphon et al. |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,648,823 B2 | 11/2003 | Thompson |
| 6,658,294 B1 | 12/2003 | Zadeh et al. |
| 6,662,053 B2 | 12/2003 | Borkan |
| 6,669,687 B1 * | 12/2003 | Saadat ............. 606/14 |
| 6,671,556 B2 | 12/2003 | Osorio et al. |
| 6,684,105 B2 | 1/2004 | Cohen et al. |
| 6,687,538 B1 | 2/2004 | Hrdlicka et al. |
| 6,690,974 B2 | 2/2004 | Archer et al. |
| 6,711,440 B2 | 3/2004 | Deal et al. |
| 6,718,203 B2 | 4/2004 | Weiner et al. |
| 6,718,207 B2 | 4/2004 | Connelly |
| 6,721,600 B2 | 4/2004 | Jorgenson et al. |
| 6,721,603 B2 | 4/2004 | Zabara et al. |
| 6,725,092 B2 | 4/2004 | MacDonald et al. |
| 6,731,979 B2 | 5/2004 | MacDonald |
| 6,745,077 B1 | 6/2004 | Griffith et al. |
| 6,754,539 B1 | 6/2004 | Erickson et al. |
| 6,757,566 B2 | 6/2004 | Weiner et al. |
| 6,760,624 B2 | 7/2004 | Anderson et al. |
| 6,760,625 B1 | 7/2004 | Kroll |
| 6,760,628 B2 | 7/2004 | Weiner et al. |
| 6,763,268 B2 | 7/2004 | MacDonald et al. |
| 6,778,856 B2 | 8/2004 | Connelly et al. |
| 6,792,316 B2 | 9/2004 | Sass |
| 6,795,730 B2 | 9/2004 | Connelly et al. |
| 6,795,736 B2 | 9/2004 | Connelly et al. |
| 6,799,069 B2 | 9/2004 | Weiner et al. |
| 6,804,557 B1 | 10/2004 | Kroll |
| 6,819,954 B2 | 11/2004 | Connelly |
| 6,819,958 B2 | 11/2004 | Weiner et al. |
| 6,829,509 B1 | 12/2004 | MacDonald et al. |
| 6,843,870 B1 * | 1/2005 | Bluger ............. 156/50 |
| 6,845,266 B2 | 1/2005 | Weiner et al. |
| 6,850,805 B2 | 2/2005 | Connelly et al. |
| 6,875,180 B2 | 4/2005 | Weiner et al. |
| 6,901,290 B2 | 5/2005 | Foster et al. |
| 6,906,256 B1 * | 6/2005 | Wang ............. 174/36 |
| 6,907,295 B2 | 6/2005 | Gross et al. |
| 6,920,357 B2 | 7/2005 | Osorio et al. |
| 6,925,328 B2 | 8/2005 | Foster et al. |
| 6,944,489 B2 * | 9/2005 | Zeijlemaker et al. ......... 600/373 |
| 6,949,929 B2 | 9/2005 | Gray et al. |
| 6,954,674 B2 | 10/2005 | Connelly |
| 6,961,618 B2 | 11/2005 | Osorio et al. |
| 6,985,775 B2 | 1/2006 | Reinke et al. |
| 6,993,387 B2 | 1/2006 | Connelly et al. |

| | | |
|---|---|---|
| 7,006,859 B1 | 2/2006 | Osorio et al. |
| 7,010,357 B2 | 3/2006 | Helfer et al. |
| 7,013,174 B2 | 3/2006 | Connelly et al. |
| 7,015,393 B2 | 3/2006 | Weiner et al. |
| 7,047,074 B2 | 5/2006 | Connelly et al. |
| 7,054,686 B2 | 5/2006 | MacDonald |
| 7,107,097 B2 | 9/2006 | Stern et al. |
| 7,123,013 B2 | 10/2006 | Gray |
| 7,171,166 B2 | 1/2007 | Ng et al. |
| 7,174,219 B2 * | 2/2007 | Wahlstrand et al. ........... 607/116 |
| 7,212,869 B2 | 5/2007 | Wahlstrom et al. |
| 7,221,981 B2 | 5/2007 | Gliner |
| 7,239,924 B2 | 7/2007 | Kolberg |
| 7,289,856 B1 * | 10/2007 | Karicherla .................... 607/122 |
| 7,584,004 B2 | 9/2009 | Caparso et al. |
| 2002/0072782 A1 | 6/2002 | Osorio et al. |
| 2003/0083726 A1 * | 5/2003 | Zeijlemaker et al. ......... 607/122 |
| 2003/0195601 A1 | 10/2003 | Hung et al. |
| 2004/0015205 A1 | 1/2004 | Whitehurst et al. |
| 2004/0147992 A1 | 7/2004 | Bluger et al. |
| 2004/0167583 A1 | 8/2004 | Knudson et al. |
| 2004/0172088 A1 | 9/2004 | Knudson et al. |
| 2004/0210291 A1 * | 10/2004 | Erickson et al. .............. 607/117 |
| 2005/0015128 A1 | 1/2005 | Rezai et al. |
| 2005/0016657 A1 | 1/2005 | Bluger |
| 2005/0107858 A1 | 5/2005 | Bluger |
| 2005/0154426 A1 * | 7/2005 | Boveja et al. .................. 607/45 |
| 2005/0154435 A1 | 7/2005 | Stern et al. |
| 2005/0222642 A1 * | 10/2005 | Przybyszewski et al. ...... 607/48 |
| 2005/0251212 A1 * | 11/2005 | Kieval et al. ...................... 607/2 |
| 2005/0272280 A1 | 12/2005 | Osypka |
| 2006/0058597 A1 | 3/2006 | Machado et al. |
| 2006/0106430 A1 | 5/2006 | Fowler et al. |
| 2006/0167497 A1 | 7/2006 | Armstrong et al. |
| 2006/0173493 A1 | 8/2006 | Armstrong et al. |
| 2006/0184211 A1 | 8/2006 | Gaunt et al. |
| 2006/0224199 A1 | 10/2006 | Zeijlemaker et al. |
| 2006/0253164 A1 | 11/2006 | Zhang et al. |
| 2006/0265025 A1 | 11/2006 | Goetz et al. |
| 2007/0027497 A1 | 2/2007 | Parnis et al. |
| 2007/0027498 A1 | 2/2007 | Maschino et al. |
| 2007/0027500 A1 | 2/2007 | Maschino et al. |
| 2007/0032834 A1 | 2/2007 | Gliner et al. |
| 2007/0060991 A1 * | 3/2007 | North et al. .................... 607/117 |
| 2007/0073150 A1 | 3/2007 | Gopalsami et al. |
| 2007/0100392 A1 | 5/2007 | Maschino et al. |
| 2007/0142889 A1 | 6/2007 | Whitehurst et al. |
| 2007/0173902 A1 | 7/2007 | Maschino et al. |
| 2007/0179557 A1 | 8/2007 | Maschino et al. |
| 2007/0179579 A1 * | 8/2007 | Feler et al. ..................... 607/117 |
| 2007/0179584 A1 | 8/2007 | Gliner |
| 2008/0033503 A1 | 2/2008 | Fowler et al. |
| 2008/0046035 A1 | 2/2008 | Fowler et al. |
| 2008/0071323 A1 | 3/2008 | Lowry et al. |
| 2008/0200925 A1 | 8/2008 | Johnson |
| 2008/0215110 A1 | 9/2008 | Gunderson et al. |
| 2008/0255582 A1 | 10/2008 | Harris |
| 2009/0076567 A1 | 3/2009 | Fowler et al. |
| 2009/0240296 A1 * | 9/2009 | Zeijlemaker et al. .............. 607/5 |

OTHER PUBLICATIONS

Mesut Sahin, Improved Nerve Cuff Electrode Recordings with Subthreshold Anodic Currents, IEEE Transactions on Biomedical Engineering, Aug. 1998, pp. 1044-1050, vol. 45, No. 8.

Peter J. Basser and Bradley J. Roth, New Currents in Electrical Stimulation of Excitable Tissues, Annu. Rev. Biomed. Eng. 2000, vol. 2, pp. 377-397.

* cited by examiner

Foldable Member (810)

Opened After Implantation

Foldable Member (810)

Closed Before Implantation

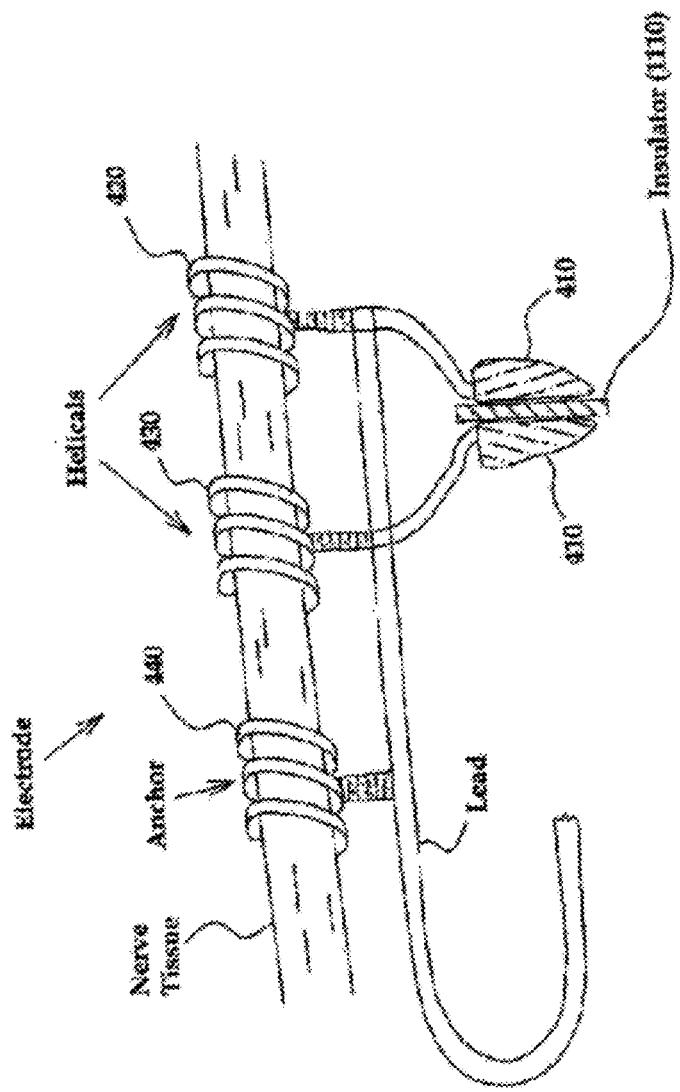

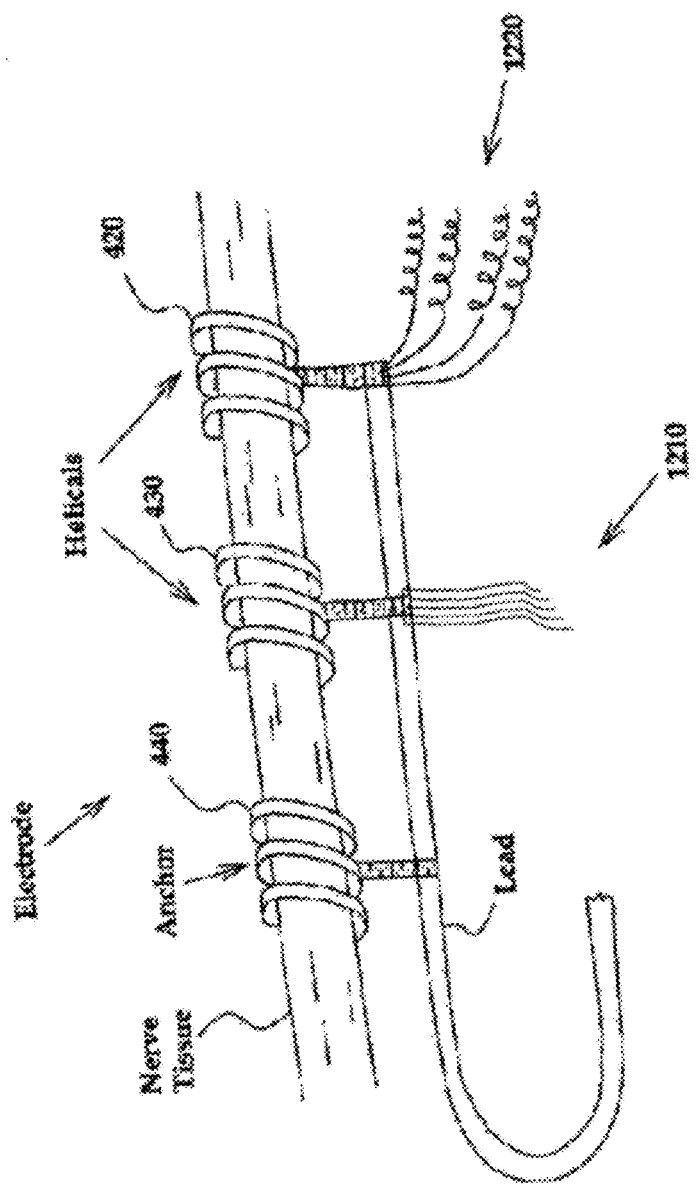

HEAT DISSIPATION FOR A LEAD ASSEMBLY

BACKGROUND OF THE INVENTION

1. Field of the Invention

This invention relates generally to implantable lead assemblies, and, more particularly, to lead assemblies providing improved heat dissipation at an end of the lead having an adjacent electrode. The improved lead reduces or eliminates tissue damage to body structures coupled to the electrode. The lead assembly may be coupled to an implantable medical device (IMD).

2. Description of the Related Art

The human nervous system (HNS) includes the brain and the spinal cord, collectively known as the central nervous system (CNS), and the nerves in the remainder of the body, which collectively form the peripheral nervous system (PNS). The central nervous system comprises nerve fibers that transmit nerve signals to, from, and within the brain and spinal cord. The peripheral nervous system includes nerves that connect the brain to the rest of the body and provide sensory, motor, and other neural signals. The PNS includes the cranial nerves, which connect directly to the brain to control, for example, vision, eye movement, hearing, facial movement, and feeling. The PNS also includes the autonomic nervous system (ANS), which controls such involuntary functions as blood vessel diameter, intestinal movements, and actions of many internal organs. Autonomic functions include blood pressure, body temperature, heartbeat and essentially all the unconscious activities that occur without voluntary control.

Many, but not all, nerve fibers in the brain and the peripheral nerves are sheathed in a covering called myelin. The myelin sheath insulates electrical pulses traveling along the nerves. A nerve bundle may comprise up to 100,000 or more individual nerve fibers of different types, including larger diameter A and B fibers which comprise a myelin sheath and C fibers which have a much smaller diameter and are unmyelinated. Different types of nerve fibers, among other things, comprise different sizes, conduction velocities, stimulation thresholds, and myelination status (i.e., myelinated or unmyelinated).

As used herein, "stimulation" or "stimulation signal" refers to the application of an electrical, mechanical, magnetic, electromagnetic, photonic, audio and/or chemical signal to a neural structure in the patient's body. The signal is an exogenous signal that is distinct from the endogenous electrical, mechanical, and chemical activity (e.g., afferent and/or efferent electrical action potentials) generated by the patient's body and environment. In other words, the stimulation signal (whether electrical, mechanical, magnetic, electro-magnetic, photonic, audio or chemical in nature) applied to the nerve in the present invention is a signal applied from an artificial source, e.g., a neurostimulator.

A "therapeutic signal" refers to a stimulation signal delivered to a patient's body with the intent of treating a disorder by providing a modulating effect to neural tissue. The effect of a stimulation signal on neuronal activity is termed "modulation"; however, for simplicity, the terms "stimulating" and "modulating", and variants thereof, are sometimes used interchangeably herein. In general, however, the delivery of an exogenous signal itself refers to "stimulation" of the neural structure, while the effects of that signal, if any, on the electrical activity of the neural structure are properly referred to as "modulation." The effect of delivery of the stimulation signal to the neural tissue may be excitatory or inhibitory and may potentiate acute and/or long-term changes in neuronal activity. For example, the "modulating" effect of the stimulation signal to the neural tissue may comprise one more of the following effects: (a) changes in neural tissue to initiate an action potential (afferent and/or efferent action potentials); (b) inhibition of conduction of action potentials (whether endogenous or exogenously induced) or blocking the conduction of action potentials (hyperpolarizing or collision blocking), (c) affecting changes in neurotransmitter/neuromodulator release or uptake, and (d) changes in neuro-plasticity or neurogenesis of brain tissue.

Thus, electrical neurostimulation or modulation of a neural structure refers to the application of an exogenous electrical signal (as opposed to mechanical, chemical, photonic, or another mode of signal delivery) to the neural structure. Electrical neurostimulation may be provided by implanting an electrical device underneath the skin of a patient and delivering an electrical signal to a nerve such as a cranial nerve. In one embodiment, the electrical neurostimulation involves sensing or detecting a body parameter, with the electrical signal being delivered in response to the sensed body parameter. This type of stimulation is generally referred to as "active," "feedback," or "triggered" stimulation. In another embodiment, the system may operate without sensing or detecting a body parameter once the patient has been diagnosed with a medical condition that may be treated by neurostimulation. In this case, the system may periodically apply a series of electrical pulses to the nerve (e.g., a cranial nerve such as a vagus nerve) intermittently throughout the day, or over another predetermined time interval. This type of stimulation is generally referred to as "passive," "non-feedback," or "prophylactic," stimulation. The stimulation may be applied by an implantable medical device that is implanted within the patient's body. In another alternative embodiment, the signal may be generated by an external pulse generator outside the patient's body, coupled by an RF or wireless link to an implanted electrode.

Generally, neurostimulation signals to perform neuromodulation are delivered by the implantable device via one or more leads. The leads generally terminate into electrodes, which are affixed onto a tissue in the patient's body. A number of leads may project from an implantable device onto various portions of a patient's body. For example, a number of electrodes may be attached to various points of a nerve or other tissue inside a human body for delivery of neurostimulation.

Occasionally, a patient having an implantable medical device may be subjected to an electrical field, a magnetic field, and/or an electromagnetic field. When an implanted medical system is subjected to one of the aforementioned fields, a coupled signal and/or noise may appear on various portions the implantable medical system, particularly on the leads and electrodes. Depending on the strength of the field, a significant amount of coupled energy may appear on the leads. This coupled energy may cause adverse effects, such as heating of various portions of the implantable system. This heating may damage tissue that is proximate to the portion of the implantable system that experiences the thermal changes.

Turning to FIG. 1, a stylized diagram of a prior art electrode in contact with body tissue is illustrated. The electrode includes a tip end. The electrode may experience an induced current that may flow in the direction indicated in FIG. 1. The induced current ($i_{induced}$) may be the result of an electrical field, a magnetic field, or an electromagnetic field applied to the electrode. The induced current may flow through a lead connected at a proximal end to the IMD and at a distal end to the electrode. At the tip of the electrode, the current path is interrupted and the induced current may experience a significant sudden increase in impedance (Imp). The power experienced by the body tissue at the tip end of the electrode is defined by Equation 1.

$$\text{Power} = (i_{induced})^2 * \text{Imp} \qquad \text{Equation 1}$$

The power relating to the current that is induced may be significantly large since it is equal to the square of the induced current $[(i_{induced})^2]$ multiplied by the high impedance [Imp] at the tip end of the electrode. Therefore, at the intersection of the body tissue and the electrode, a significantly high amount of power may be delivered. Due to the principle of conservation of energy, this power may be converted into and dissipated as another form of energy, such as thermal energy. In other words, at the tip of the electrode a large amount of power is transformed to thermal energy, thereby causing a significant rise in temperature.

Turning now to FIG. 2, a graph relating to an exemplary temperature rise resulting from an induced current is illustrated. After the start-of-scan of a radio frequency (RF) signal, the tip of the electrode associated with the IMD may experience induced current. As described above, this induced current may result in significant thermal energy associated with power flux at the electrode-tissue interface. In some cases, the temperature at the interface may rise asymptotically until a substantial steady-state is reached. For example, as illustrated in FIG. 2, upon the start-of-scan, a significantly rapid rise in the temperature at the end of the electrode may occur. In one example, a temperature rise above 42° C. may be experienced in a relatively short time interval. Due to this sudden rise in temperature, the tissue surrounding the electrode may be damaged, perhaps irreparably. Thus, nerve damage may occur because of the thermal energy dissipated into a nerve tissue coupled to the electrode of FIG. 1. State-of-the-art implantable device systems generally lack an efficient method of protecting body tissue from thermal damage due to RF or magnetic energy induced current.

The present invention is directed to overcoming, or at least reducing, the effects of one or more of the problems set forth above.

SUMMARY OF THE INVENTION

In one aspect, the present invention comprises an electrode system for delivering an electrical signal to a first tissue of a patient's body. The system comprises a lead and an electrode coupled to the lead. The electrode includes a stimulation portion that couples to the first tissue to deliver an electrical signal to the first tissue. The electrode also includes a dissipation portion that does not interface with the first tissue and is branching off the lead along a distal branch. The dissipation portion is adapted to interface with a second tissue. The dissipation portion is adapted to dissipate thermal energy away from the electrode.

In another aspect, the present invention comprises a neurostimulation lead assembly for providing a neurostimulation signal to a first tissue of a patient's body. The assembly includes a lead for conducting a neurostimulation signal and an electrode operatively coupled to the lead. The electrode includes an electrical signal delivery portion that couples to the first tissue to deliver the neurostimulation signal to the first tissue. The electrode also includes a heat dissipation portion that is not interfaced with the first tissue. The heat dissipation portion is adapted to dissipate thermal energy away from the electrode.

In yet another aspect, the present invention comprises an implantable medical device system to provide an electrical signal to a portion of a patient's body to treat a disorder. The implantable medical device system includes an implantable medical device for generating an electrical signal, a lead, and an electrode operatively coupled to the implantable medical device and to the lead for delivering the electrical signal to a first tissue of a patient's body. The electrode includes an electrical signal delivery portion coupled to the first tissue to deliver the electrical signal to the first tissue. The electrode also includes a heat dissipation portion that does not interface with the first tissue. The heat dissipation portion is adapted to dissipate thermal energy away from the electrode.

In yet another aspect, the present invention comprises an electrode for delivering an electrical signal to a portion of a nerve tissue of a patient's body for treating a disorder. The electrode includes a stimulation portion that couples to the nerve tissue to deliver an electrical signal to the nerve tissue to treat a disorder. The stimulation portion includes a first helical portion to provide a cathode, a second helical portion to provide an anode, and an anchor portion to affix the stimulation portion to the nerve tissue. The electrode also includes a thermal energy dissipation portion that does not interface with the nerve tissue. The thermal energy dissipation portion includes at least one heat dissipation element to dissipate thermal energy away from the electrode. The thermal energy dissipation portion is substantially surrounded by an insulating barrier.

In yet another aspect, the present invention comprises an electrode system for delivering an electrical signal to a first tissue of a patient's body. The system comprises a lead and an electrode coupled to the lead. The electrode includes a stimulation portion that couples to the first tissue to deliver an electrical signal to the first tissue. The stimulation portion is not an end portion of the electrode. The electrode also includes a dissipation portion that interfaces with a second tissue. The dissipation portion is adapted to dissipate thermal energy from the electrode to the second tissue.

In another aspect, the present invention comprises an electrode system for sensing an electrical signal in a first tissue of a patient's body. The system includes a lead and an electrode coupled to the lead. The electrode includes a sensing portion that couples to the first tissue to sense an electrical signal to the first tissue. The electrode also includes a dissipation portion that does not couple to the first tissue. The dissipation portion is adapted to dissipate thermal energy away from the electrode.

BRIEF DESCRIPTION OF THE DRAWINGS

The invention may be understood by reference to the following description taken in conjunction with the accompanying drawings, in which like reference numerals identify like elements, and in which:

FIG. 11 illustrates an electrode/lead assembly that includes a capacitive coupling configuration of heat dissipation apparatuses, in accordance with another illustrative embodiment of the present invention; and FIG. 12 illustrates an electrode/lead assembly that includes a vein configuration of the heat dissipation apparatuses, in accordance with another illustrative embodiment of the present invention.

Figure 1:
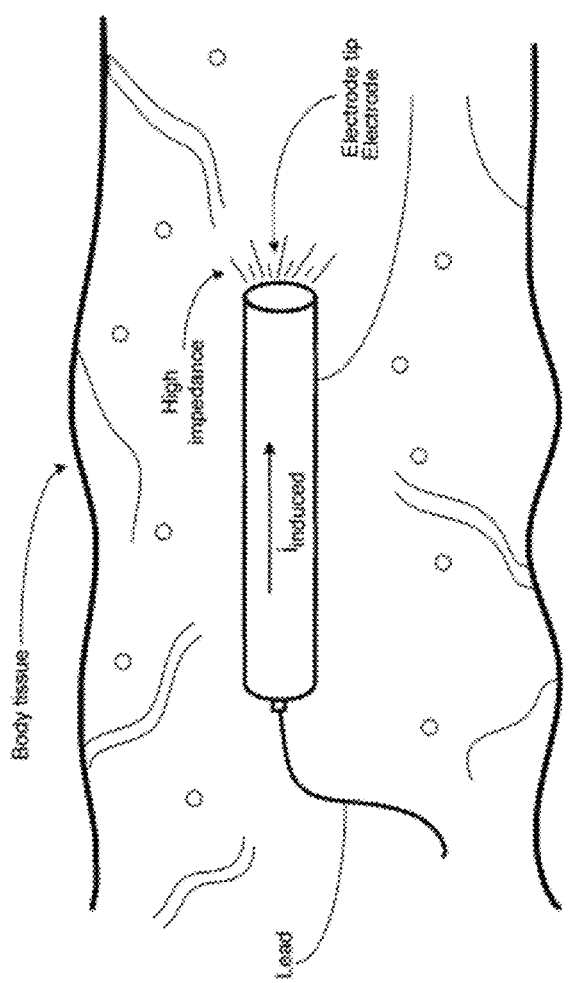
FIG. 1 illustrates a stylized diagram of a prior art electrode in contact with body tissue, wherein an induced current is found at the tip of the electrode.
Figure 2:
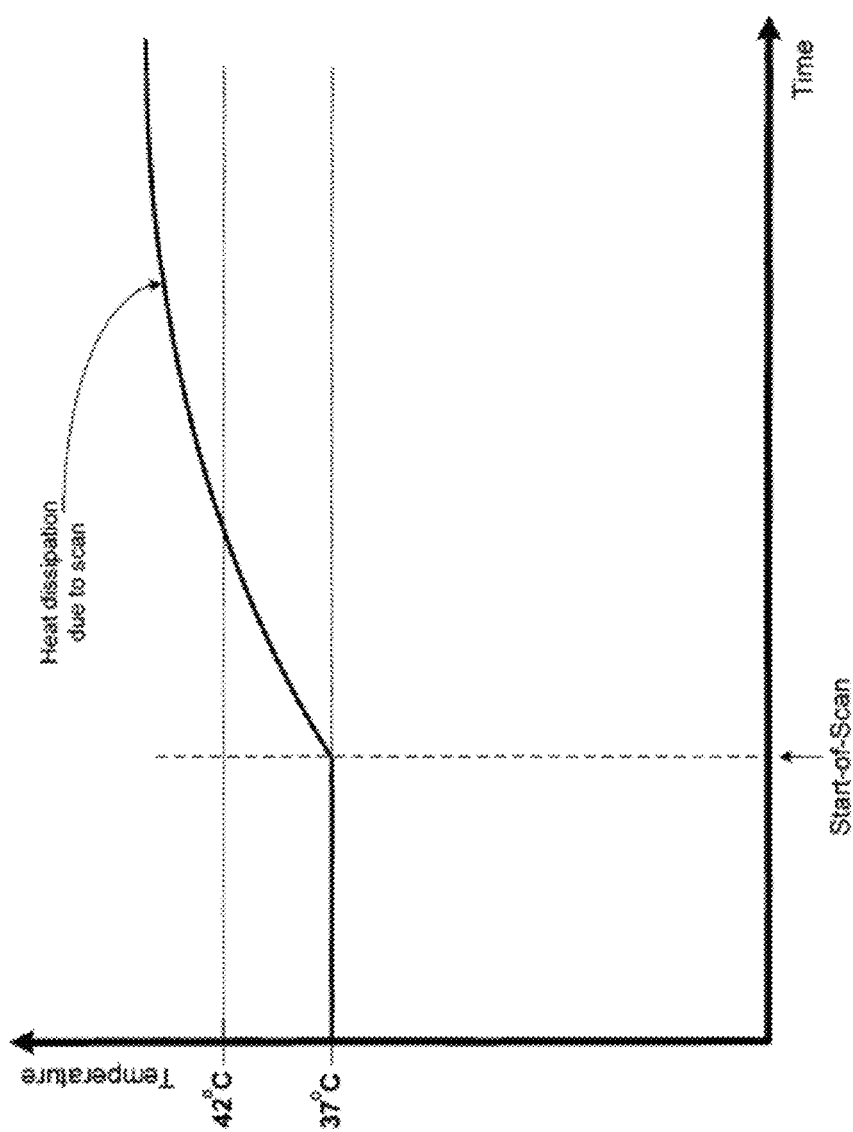
FIG. 2 illustrates a graph depicting an exemplary rise in temperature resulting from induced current.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

Certain terms are used throughout the following description and claims refer to particular system components. As one skilled in the art will appreciate, components may be referred to by different names. This document does not intend to distinguish between components that differ in name but not function. In the following discussion and in the claims, the terms "including" and "including" are used in an open-ended fashion, and thus should be interpreted to mean "including, but not limited to." Also, the term "couple" or "couples" is intended to mean either a direct or an indirect electrical connection. For example, if a first device couples to a second device, that connection may be through a direct electrical connection or through an indirect electrical connection via other devices, biological tissues, electric (e.g., as in capacitive) or magnetic fields. "Direct contact," "direct attachment," or providing a "direct coupling" indicates that a surface of a first element contacts the surface of a second element with no substantial attenuating medium therebetween. The presence of substances, such as bodily fluids, that do not substantially attenuate electrical connections does not vitiate direct contact. The word "or" is used in the inclusive sense (i.e., "and/or") unless a specific use to the contrary is explicitly stated.

As used herein, "stimulation" or "stimulation signal" refers to the application of an electrical, mechanical, and/or chemical signal to a neural structure in the patient's body. In one embodiment, the stimulation comprises an electrical signal. The stimulation signal may induce afferent and/or efferent action potentials on the nerve, may block native afferent and/or efferent action potentials, or may be applied at a sub-threshold level that neither generates action potentials nor blocks native action potentials. In one embodiment, the stimulation signal is a signal that is capable of inducing afferent and/or efferent action potentials on the nerve.

The stimulation signal applied to the neural structure in embodiments of the present invention refers to an exogenous signal that is distinct from the endogenous electrical, mechanical, and chemical activity (e.g., afferent and/or efferent electrical action potentials) generated by the patient's body and environment. In other words, the stimulation signal (whether electrical, mechanical or chemical in nature) applied to the nerve in the present invention is a signal applied from an artificial source, e.g., a neurostimulator.

The term "electrode" or "electrodes" described herein may refer to one or more stimulation electrodes, one or more sensing electrodes, and/or to one or more electrodes that are capable of delivering a stimulation signal as well as performing a sensing function. Stimulation electrodes may refer to an electrode that is capable of delivering a stimulation signal to a tissue of a patient's body. A sensing electrode may refer to an electrode that is capable of sensing a physiological indication of a patient's body. The physiological indication may include an indication of a patient's heart rate, blood pressure, blood glucose, etc. In some embodiments, the term "electrode" and/or "electrodes" may refer to an electrode or a set of electrodes that are capable of delivering a stimulation signal as well as sensing a physiological indication.

As used herein, the terms "stimulating" and "stimulator" may generally refer to delivery of a stimulation signal to a neural structure. The effect of such stimulation on neuronal activity is termed "modulation"; however, for simplicity, the terms "stimulating" and "modulating", and variants thereof, are sometimes used interchangeably herein. In general, however, the delivery of an exogenous signal refers to "stimulation" of the neural structure, while the effects of that signal, if any, on the electrical activity of the neural structure are properly referred to as "modulation." The effect of delivery of the stimulation signal to the neural tissue may be excitatory or inhibitory and may potentiate acute and/or long-term changes in neuronal activity. For example, the "modulating" effect of the stimulation signal to the neural tissue may comprise one more of the following effects: (a) changes in neural tissue to initiate an action potential (bi-directional or uni-directional); (b) inhibition of conduction of action potentials (endogenous or externally stimulated) or blocking the conduction of action potentials (hyperpolarizing or collision blocking), (c) affecting changes in neurotransmitter/neuromodulator release or uptake, and (d) changes in neuro-plasticity or neurogenesis of brain tissue.

Cranial nerve stimulation has been proposed to treat a number of nervous system disorders, including epilepsy and other movement disorders, mood and other neuropsychiatric disorders, dementia, coma, migraine headache, obesity, eating disorders, sleep disorders, cardiac disorders (such as congestive heart failure and atrial fibrillation), hypertension, endocrine disorders (such as diabetes and hypoglycemia), and pain, among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the recognition that cranial nerve stimulation may be an appropriate treatment for the foregoing conditions, the fact that detailed neural pathways for many (if not all) cranial nerves remain relatively unknown makes predictions of efficacy for any given disorder difficult. Even if such pathways were known, moreover, the precise stimulation parameters that would energize particular pathways that affect the particular disorder likewise are difficult to predict.

In one embodiment of the present invention, methods, apparatus, and systems stimulate an autonomic nerve, such as a cranial nerve, e.g., a vagus nerve, using an electrical signal to treat an eating disorder. "Electrical signal" on the nerve refers to the electrical activity (i.e., afferent and/or efferent action potentials) that are not generated by the patient's body and environment, rather applied from, an artificial source, e.g., an implanted neurostimulator. Disclosed herein is a method for treating an eating disorder using stimulation of the vagus nerve (cranial nerve X). Other types of eating disorders include, but are not limited to, bulimia nervosa, anorexia nervosa, compulsive and binge eating, and obesity. Bulimia nervosa ("bulimia") is an eating disorder in which an individual experiences recurrent episodes of insatiable craving for food often resulting in episodes of binge eating followed by inappropriate compensatory behavior to prevent weight gain. The inappropriate compensatory behavior typically includes self-induced vomiting, fasting, excessive exercise, and use of laxatives and diuretics. People suffering from bulimia commonly engage in binge eating and inappropriate compensatory behavior an average of two times a week for a period of three or more months. Treatments to address these disorders include physiological treatments, as well as psychological and psychiatric treatments. Besides drug regimens, invasive medical procedures, and/or counseling, effective treatment of such diseases and disorders are somewhat limited. Further, certain patients may not react favorably to various types of drugs or other treatments. A generally suitable form of neurostimulator for use in the method and apparatus of the present invention is disclosed, for example, in U.S. Pat. No. 5,154,172, assigned to the same assignee as the present application. The neurostimulator may be referred to a NeuroCybernetic Prosthesis (NCP®, Cyberonics, Inc., Houston, Tex., the assignee of the present application). Certain parameters of the electrical stimulus generated by the neurostimulator are programmable, such as be means of an external programmer in a manner conventional for implantable electrical medical devices.

In one embodiment, treatment of neuropsychiatric mood disorders is proposed. Mood disorders for which treatment is contemplated include, but are not limited to, depression, major depressive disorder, bipolar disorder, dysthymic disorder, anxiety disorders. Anxiety disorders include, but are not limited to, obsessive compulsive disorder (OCD), post-traumatic stress syndrome (PTSD), panic disorder, generalized anxiety, simple phobia and social phobia. For ease of reference, the use of the term "mood disorder" herein also includes the above-named disorders.

Yet another embodiment includes treatment of a disorder of the endocrine stress system. This includes disorders associated with the hypothalmus-pitituary-adrenal (HPA) axis and sympathetic-adrenal medullary (SAM) axis and includes, but is not limited to, disorders of the hormone system, energy metabolism-related disorders, and reproductive disorders.

Implantable medical devices that are implanted in a patient's body also have accompanying leads and electrodes attached for delivering therapeutic, electrical signals from the IMD to various targeted portions of the patient's body. Occasionally, a patient having an IMD implanted may be exposed to a significant electrical field, magnetic field, and/or electromagnetic field. These fields may cause a radio frequency (RF) induced current to flow through the lead(s) and electrode(s). For example, if a patient is exposed to a magnetic resonance imaging (MRI) process, significant amounts of RF induced currents may be formed in the implantable medical system.

The inducement of the RF current in the leads and/or electrodes may cause RF induced heating. The heating may adversely affect the lead and electrode as well as the surrounding tissues. The lead may act as an antenna that is conductive in an RF field. This antenna effect may produce significant amount of induced current, especially at the tip of the conductor(s). The induced current may cause significant amounts of RF energy to be converted to thermal energy at various portions of the lead/electrode assembly, e.g., the tip of the lead/electrode assembly. Embodiments of the present invention provide for effectively "moving" the tip of the lead conductors beyond the electrode surfaces. Therefore, RF induced heat may be moved away from the electrodes and the tissue upon which the electrode is coupled, such as the vagus nerve. By effectively reconfiguring the electrode tip into a large surface area using one or more heat dissipation apparatuses, the thermal energy may be dissipated to a larger volume of the patient's body. This may cause significantly lower amounts of temperature increase at any given point. Many types of insulating material may be used to substantially surround the heat dissipation apparatus. The insulation may be comprised of various materials and may provide thermal and/or electrical protection. The insulation in one embodiment may be a material that is transparent to an RF signal. One example of the insulating material is NuSil.

Embodiments of the present invention provide for redirecting thermal energy that may be induced upon a lead and an electrode associated with an implantable medical system described below. Current induced by an external source, such as an RF signal, may cause a significant amount of induced energy in a lead/electrode assembly. This energy may be dissipated using the heat-release apparatus provided by embodiments of the present invention. Therefore, thermal energy may be directed away from the electrode components, such as the positive and negative terminals of the electrodes. This may provide for reduced damage to nerve or other body tissue components.

Embodiments of the present invention provide for apparatuses with varying shapes to be used for dissipating thermal energy away from components attached to sensitive portions of a human body. Embodiments of the present invention also provide for a collapsible and expandable heat apparatus that may be inserted into a collapsed configuration and may expand once implanted into the patient's body. This expansion may be manually directed, electronically controlled, and/or automatically expanded based upon reaching a predetermined temperature, such as normal human body temperature.

Further, embodiments of the present invention provide for utilizing a heat dissipation apparatus in combination with a filter, such as an RF filter. This combination may provide for a current path to prompt the induced current to flow towards the heat dissipation apparatus. Therefore, the RF filter may reduce the amount of RF induced current traveling to various portions of the electrode, such as the helical terminals and/or the anchor portions of the electrode. Utilizing the RF filters provided herein, various targeted electrical signals may be prevented from effecting the operation of the lead or providing thermal energy to the electrode. Therefore, the RF filter may direct the RF induced current to the heat dissipation apparatus.

Still further, embodiments of the present invention provide for utilizing a thermal insulating material on the surface of the heat dissipation apparatus to allow for a slow dissipation of thermal energy. The insulation encapsulating a heat dissipation apparatus provides for dissipating heat at a relatively low rate. Further, the insulated material may comprise electrical insulation for a reduced amount of current to flow. In an alternative embodiment, the heat dissipation apparatus may comprise a thermal insulator as well as an electrical insulator. Embodiments of the present invention provide for slower release of thermal energy as to reduce the possibility of damage caused by thermal energy in the patient's body. In one embodiment, the insulator may provide insulation properties at a frequency of a stimulation signal as well as a frequency of a signal that is capable of inducing thermal energy in a portion of an electrode.

Figure 3A:
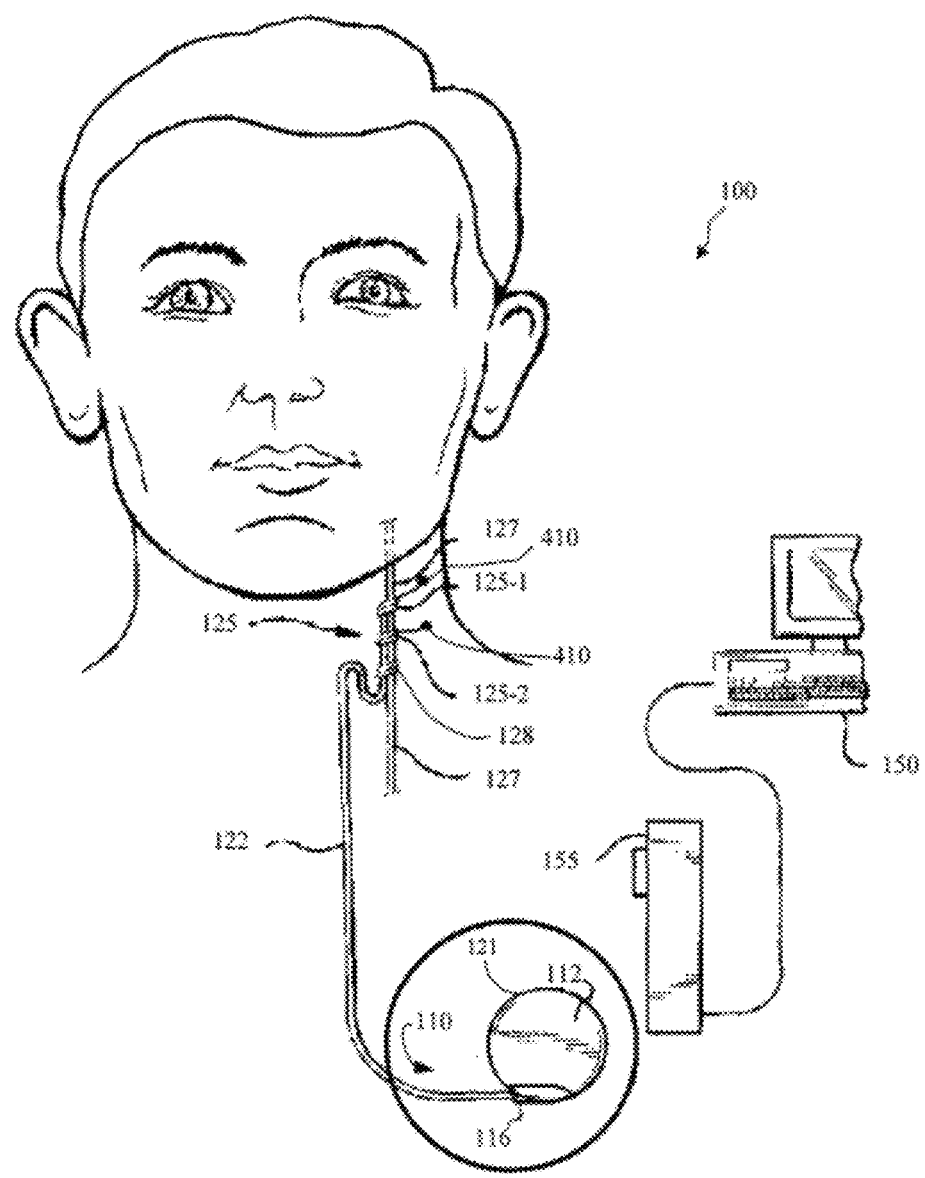
FIGS. 3A-3B provide stylized diagrams of an implantable medical device implanted into a patient's body for providing stimulation to a portion of the patient's body, in accordance with one illustrative embodiment of the present invention.
Figure 3B:
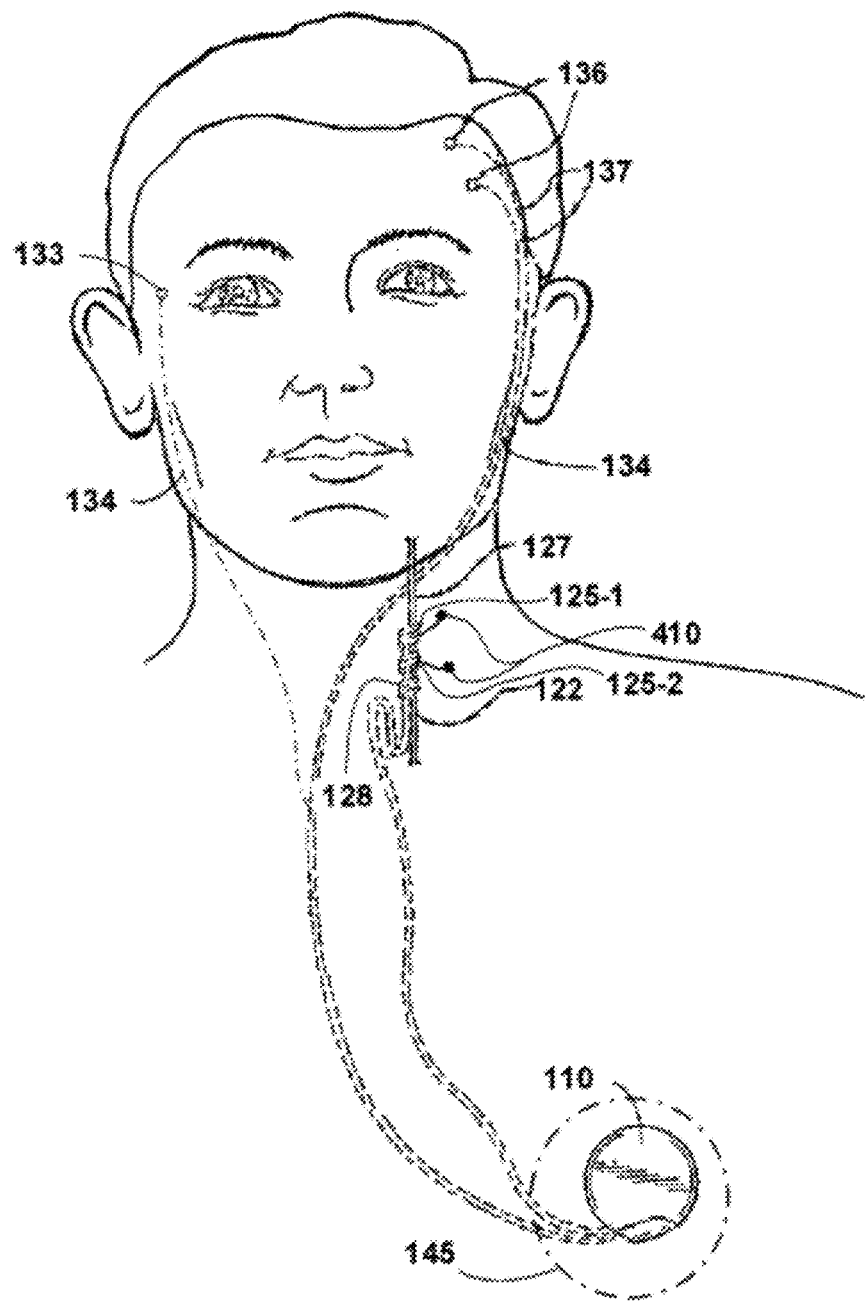

Although not so limited, a system capable of implementing embodiments of the present invention is described below. FIGS. 3A-3B depict a stylized implantable medical system 100 for implementing one or more embodiments of the present invention. FIGS. 3A-3B illustrate an electrical signal generator 110 having main body 112 comprising a case or shell 121 with a header 116 (FIG. 3A) for connecting to leads 122. The generator 110 is implanted in the patient's chest in a pocket or cavity formed by the implanting surgeon just below the skin (indicated by a dotted line 145, FIG. 3B), similar to the implantation procedure for a pacemaker pulse generator.

A stimulating nerve electrode assembly 125, preferably comprising an electrode pair, is conductively connected to the distal end of an insulated, electrically conductive lead assembly 122, which preferably comprises a pair of lead wires (one wire for each electrode of an electrode pair). In one embodiment, the electrode assembly 125 may comprise one or more heat dissipation apparatuses that are described in further details below. Lead assembly 122 is attached at its proximal end to connectors on the header 116 on case 121. The electrode assembly 125 may be surgically coupled to a vagus nerve 127 in the patient's neck or at another location, e.g., near the patient's diaphragm. Other cranial nerves may also be used to deliver the electrical neurostimulation signal. The electrode assembly 125 preferably comprises a bipolar stimulating electrode pair 125-1, 125-2 (FIG. 3A), such as the electrode pair described in U.S. Pat. No. 4,573,481 issued Mar. 4, 1986 to Bullara. Suitable electrode assemblies are available from Cyberonics, Inc., Houston, Tex., USA as the Model 302 electrode assembly. However, persons of skill in the art will appreciate that many electrode designs could be used in the present invention. The two electrodes are preferably wrapped about the vagus nerve, and the electrode assembly 125 may be secured to the nerve 127 by a spiral anchoring tether 128 (FIG. 3A) such as that disclosed in U.S. Pat. No. 4,979,511 issued Dec. 25, 1990 to Reese S. Terry, Jr. and assigned to the same assignee as the instant application. Lead assembly 122 is secured, while retaining the ability to flex with movement of the chest and neck, by a suture connection 130 to nearby tissue (not shown). The electrode assembly 125 may include one or more heat dissipation apparatuses 410. The heat dissipation apparatus 410 is capable of directing heat energy away from portions of the electrode assembly 125. The heat dissipation apparatus 410 is described in further details below.

In one embodiment, the open helical design of the electrode assembly 125 (described in detail in the above-cited Bullara patent), which is self-sizing and flexible, minimizes mechanical trauma to the nerve and allows body fluid interchange with the nerve. The electrode assembly 125 preferably conforms to the shape of the nerve, providing a low stimulation threshold by allowing a large stimulation contact area with the nerve. Structurally, the electrode assembly 125 comprises two electrode ribbons (not shown), of a conductive material such as platinum, iridium, platinum-iridium alloys, and/or oxides of the foregoing. The electrode ribbons are individually bonded to an inside surface of an elastomeric body portion of the two spiral electrodes 125-1 and 125-2 (FIG. 3A), which may comprise two spiral loops of a three-loop helical assembly. The lead assembly 122 may comprise two distinct lead wires or a coaxial cable whose two conductive elements are respectively coupled to one of the conductive electrode ribbons. One suitable method of coupling the lead wires or cable to the electrodes 125-1, 125-2 comprises a spacer assembly such as that disclosed in U.S. Pat. No. 5,531,778, although other known coupling techniques may be used.

The elastomeric body portion of each loop is preferably composed of silicone rubber, and the third loop 128 (which typically has no electrode) acts as the anchoring tether for the electrode assembly 125.

In certain embodiments of the invention, sensors such as eye movement sensing electrodes 133 (FIG. 3B) may be implanted at or near an outer periphery of each eye socket in a suitable location to sense muscle movement or actual eye movement. The electrodes 133 may be electrically connected to leads 134 implanted via a cannula or other suitable means (not shown) and extending along the jaw line through the neck and chest tissue to the header 116 of the electrical pulse generator 110. When included in systems of the present invention, the sensing electrodes 133 may be utilized for detecting rapid eye movement (REM) in a pattern indicative of a disorder to be treated. The detected indication of the disorder can be used to trigger active stimulation.

Other sensor arrangements may alternatively or additionally be employed to trigger active stimulation. Referring again to FIG. 3B, electroencephalograph (EEG) sensing electrodes 136 may optionally be implanted and uniformly distributed on the skull, and connected to leads 137 implanted and extending along the scalp and temple, and then connected to the electrical pulse generator 110 along the same path and in the same manner as described above for the eye movement electrode leads 134.

In alternative embodiments, temperature sensing elements and/or heart rate sensor elements may be employed to trigger active stimulation. In addition to active stimulation incorporating sensor elements, other embodiments of the present invention utilize passive stimulation to deliver a continuous, periodic or intermittent electrical signal (each of which constitutes a form of continual application of the signal) to the vagus nerve according to a programmed on/off duty cycle without the use of sensors to trigger therapy delivery. Both passive and active stimulation may be combined or delivered by a single IMD according to the present invention. Either or both modes may be appropriate to treat the particular disorder diagnosed in the case of a specific patient under observation.

The electrical pulse generator 110 may be programmed with an external computer 150 using programming software of the type copyrighted by the assignee of the instant application with the Register of Copyrights, Library of Congress, or other suitable software based on the description herein, and a programming wand 155 to facilitate radio frequency (RF)

communication between the computer 150 (FIG. 3A) and the pulse generator 110. The wand 155 and software permit non-invasive communication with the generator 110 after the latter is implanted. The wand 155 is preferably powered by internal batteries, and provided with a "power on" light to indicate sufficient power for communication. Another indicator light may be provided to show that data transmission is occurring between the wand and the generator.

A variety of stimulation therapies may be provided in implantable medical systems 100 of the present invention. Different types of nerve fibers (e.g., A, B, and C fibers being different fibers targeted for stimulation) respond differently to stimulation from electrical signals. More specifically, the different types of nerve fibers have different conduction velocities and stimulation thresholds and, therefore, differ in their responsiveness to stimulation. Certain pulses of an electrical stimulation signal, for example, may be below the stimulation threshold for a particular fiber and, therefore, may generate no action potential in the fiber. Thus, smaller or narrower pulses may be used to avoid stimulation of certain nerve fibers (such as C fibers) and target other nerve fibers (such as A and/or B fibers, which generally have lower stimulation thresholds and higher conduction velocities than C fibers). Additionally, techniques such as pre-polarization may be employed wherein particular nerve regions may be polarized before a more robust stimulation is delivered, which may better accommodate particular electrode materials. Furthermore, opposing polarity phases separated by a zero current phase may be used to excite particular axons or postpone nerve fatigue during long term stimulation.

Figure 4:
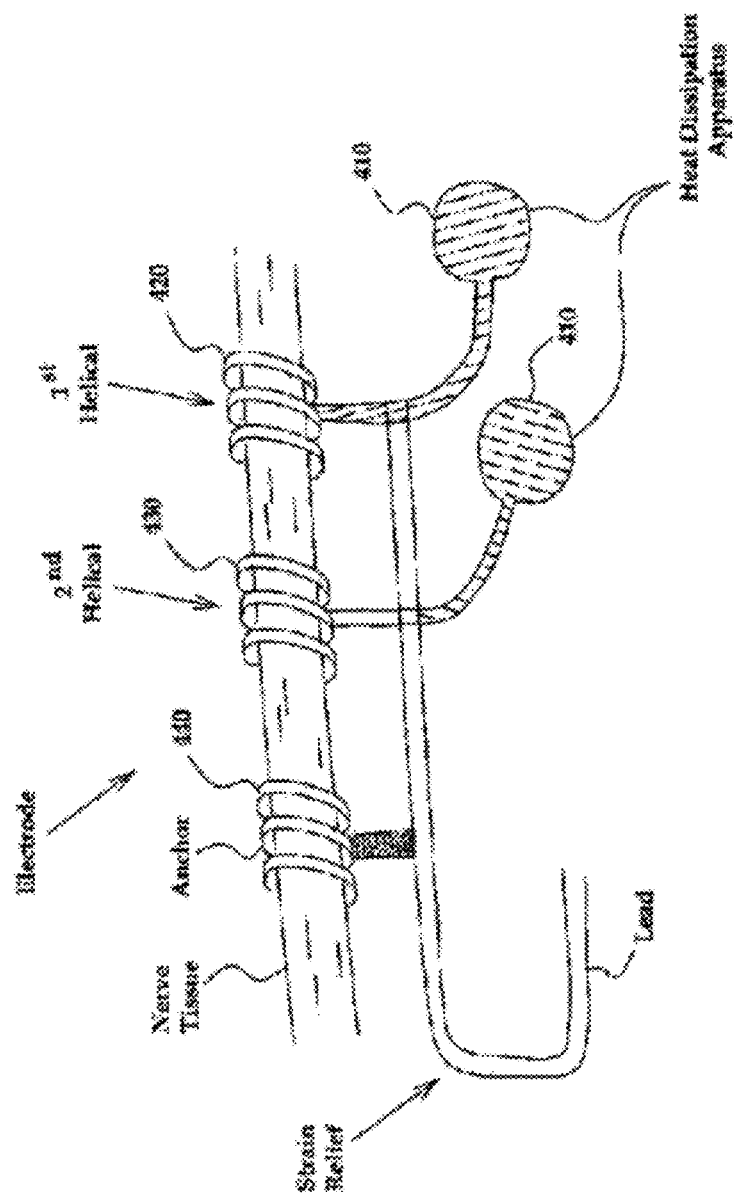
FIG. 4 provides a stylized depiction of an electrode assembly comprising a heat dissipation apparatus, in accordance with one illustrative embodiment of the present invention.

Turning now to FIG. 4, an electrode/lead assembly in accordance with one illustrative embodiment of the present invention is illustrated. A lead may be attached to an electrode which may comprise various portions. For example, the electrode may comprise a first helical 420 and a second helical 430. The helicals, 420, 430, may be electrically coupled to a portion of the patient's body, such as a nerve tissue (e.g., a cranial nerve such as the vagus nerve). The electrode may also comprise an anchor 440 that is used to affix the electrode onto the nerve tissue. In one embodiment, the first helical 420 may be a positive node and the second helical 430 may be a negative node of a neurostimulation signal that is provided by the IMD 100. Those skilled in the art having benefit of the present invention would appreciate that the positive node, the negative node, and the affixing apparatus of the electrode, which are respectively represented by the $1^{st}$ helical 420, $2^{nd}$ helical 430, and the anchor 440, may be of a variety of shapes and sizes that may be employed while remaining within the spirit and scope of the present invention.

FIG. 4 also illustrates a plurality of heat dissipation apparatuses 410. Those skilled in the art having benefit of the present disclosure would readily decipher that any number of heat dissipation apparatuses 410 may be employed while remaining within the spirit and scope of the present invention. The heat dissipation apparatus 410 is capable of directing energy away from the electrode. Therefore, the heat dissipation apparatus 410 is capable of reducing the amount of energy that would have been converted to heat near the nerve tissue, as illustrated in FIG. 4. The heat dissipation apparatus 410 may be coupled to portions of the electrode and/or to the lead itself.

The electrode is generally coupled to the lead after the strain relief portion of the lead. The heat dissipation apparatus 410 may be capable of diverting the RF current and/or RF energy that would have traveled to the various portions of the electrode. The heat dissipation apparatus 410 may comprise one or more coatings of materials, such as insulating materials. Further, details regarding the heat dissipation apparatus 410 are provided in subsequent figures and accompanying description below.

Figure 5:
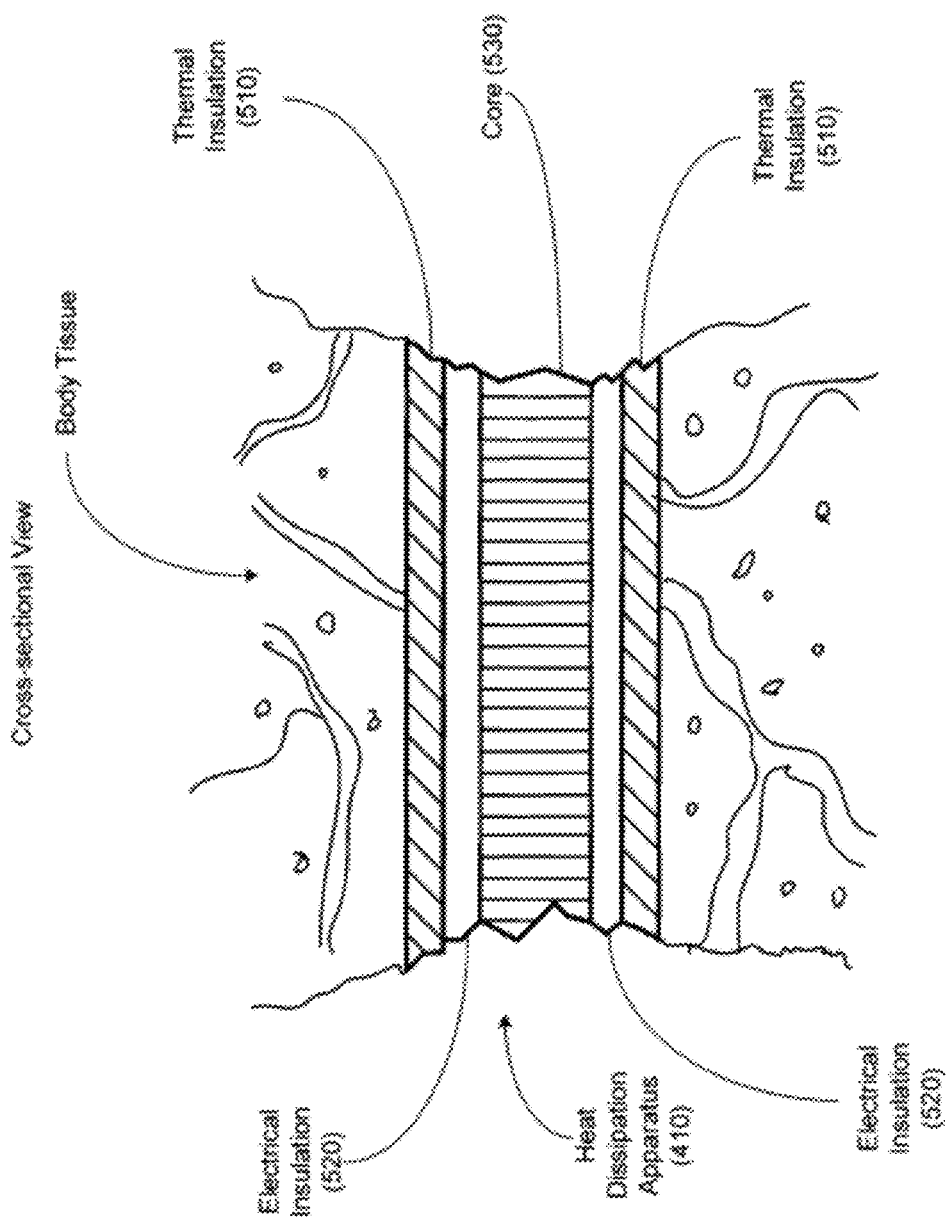
FIG. 5 depicts a cross-sectional view of the heat dissipation apparatus of FIG. 4, in accordance with one illustrative embodiment of the present invention.

Referring simultaneously to FIGS. 4 and 5, a cross-sectional stylized depiction of the heat dissipation apparatus 410 of FIG. 4, in accordance with one illustrative embodiment of the present invention, is provided. The heat dissipation apparatus 410 may comprise a core 530 that may be capable of conducting electricity and/or thermal energy. Additionally, the core 530 of the heat dissipation apparatus may be substantially encapsulated by one or more insulation materials. In one embodiment, a thermal insulation 510 may substantially encapsulate the core 530. In another embodiment, an electrical insulation 520 may substantially encapsulate the core 530. Further, in yet another embodiment, the thermal insulation material 510 and the electrical insulation 520 may substantially encapsulate the core 530. In one embodiment, the electrical insulation 520 may provide insulation properties at a frequency of the stimulation signal as well as a frequency of a signal that is capable of inducing thermal energy in a portion of an electrode. Therefore, the heat dissipation apparatus 410 is capable of directing thermal energy away from the electrode. The heat dissipation apparatus 410 is capable of providing for a slower dissipation of heat, such that no portion of the patient's body is exposed to a high temperature.

In one embodiment, the thermal insulation 510 and the electrical insulation 520 may be separate materials that are used to encapsulate the core 530 of the heat dissipation apparatus 410. In an alternative embodiment, the thermal insulation 510 and the electrical insulation 520 may be of the same material that provides the benefit of thermal insulation and electrical insulation properties.

Continuing referring to FIGS. 4 and 5, the heat dissipation apparatus 410 may comprise a structure that provides for electrical insulation as described above. Further, utilizing the benefit of the electrical insulation, the heat dissipation apparatuses 410 may be positioned in such a manner to provide an appreciable amount of capacitive coupling of the conductors associated with the heat dissipation apparatus 410. The capacitive coupling provided by the heat dissipation apparatuses 410 may provide a shunt path for high frequency signals. Therefore, during the exposure of high frequency (RF) signals, energy may be directed away from the tissues. The shunt path for high frequency energy provides for directing energy away from the tissues that are in contact with the various portions of the electrodes, such as the $1^{st}$ and $2^{nd}$ helicals 420, 430. Further details regarding the capacitive coupling embodiments of the present invention are provided below.

The exemplary illustration of the heat dissipation apparatus 410 may be modified to reflect various configurations that may be beneficial in dissipating thermal energy, as well as providing a capacitive coupling to provide a frequency shunt path away from the tissues coupled to portions of the electrode (i.e., $1^{st}$ and $2^{nd}$ helicals 420, 430). In one embodiment, the frequency shunt path may be a high frequency path. Further, the heat dissipation apparatus 410 may be a "veined" structure. The veined structure for the heat dissipation apparatus 410 may be optimized (as to the length and shape of the individual veins of the vein structure) or arranged to reduce heating at the interface between the nerve tissue and portions of the electrode. Further details relating to the veined structure are provided below.

Figure 6:
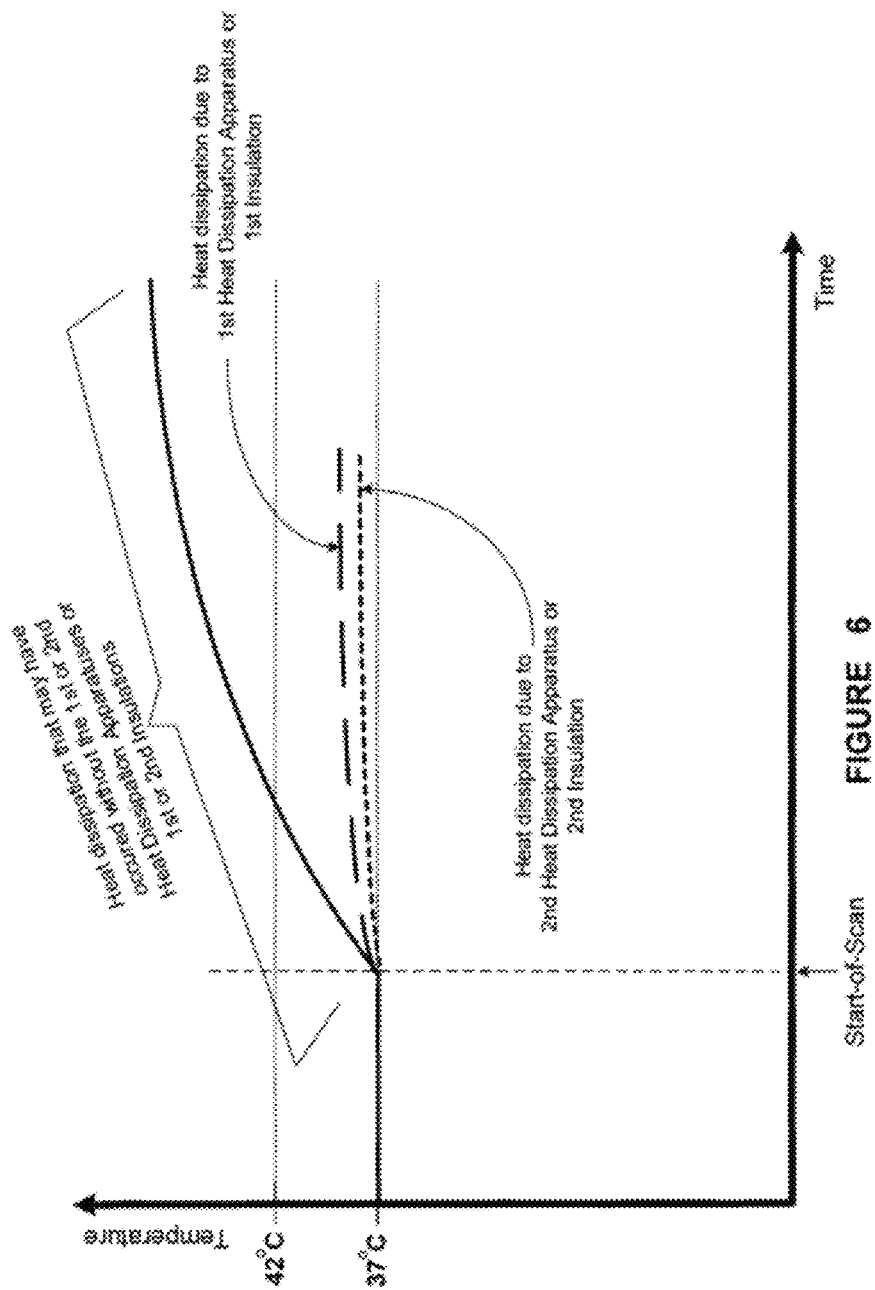
FIG. 6 illustrates a graphical illustration of a temperature diagram that includes a temperature rise curve, a first heat dissipation curve, and a second heat dissipation curve that may be caused by dissipation of induced energy.

Referring to FIG. 6, an exemplary graphical illustration of a temperature curve is provided. Upon a start-of-scan of an RF signal, the temperature rise in response to the induced current may rise at a relatively rapid pace. In one embodiment, the frequency of the stimulation signal generated by the IMD 200 may be of a substantially lower frequency than the signal that induces thermal energy in the tip points of the electrode. This higher frequency signal induce significant rise in temperature at the tip points. For example, 15 seconds after a start-of-scan from an external signal source, the temperature may rise to a level that may cause temporary or permanent tissue damage, e.g., a rise to approximately 42° C., at the ends of tip points of conductive element such as a lead wire 122 and/or electrodes 125-1 and 125-2. However, utilizing the heat dissipation apparatus 410 provided by the embodiments of the present invention, the heat or thermal energy that would normally have been present at the tip portions of the electrode (e.g., tips of the $1^{st}$ and $2^{nd}$ helicals 420, 430), may be substantially dissipated (as illustrated by the dotted curves in FIG. 6).

The rate of dissipation of thermal energy may generally be a slower rate, as compared to the temperature rise. This slower rate may be beneficial in providing the ability to contain the thermal energy and release it at a slow rate to reduce the possibility of damaging the tissue surrounding the heat dissipation apparatuses 410. This task may be achieved by providing particular shapes, such as a flat shape for the heat dissipation apparatus 410. The rate of heat dissipation due to a first type of thermal dissipation apparatus 410 or a first type of insulation, is illustrated as a curve in FIG. 6. This curve may be different from the rate of heat dissipation resulting from a second type of heat dissipation apparatus 410 or a second insulation, which may provide a more rapid dissipation of heat. Further, the heat dissipation apparatus 410 and/or the insulations are capable of dissipating thermal energy such that the possibility of excessive rise in temperature (e.g., a rise above 42° C.) at the tip points of the electrodes is substantially reduced. In one embodiment, the heat dissipation provided by embodiments of the present invention may be limited to a value below 42° C., thereby reducing the possibility of tissue damage.

In one embodiment, it may be desirable to use materials and shapes that provide for a less rapid dissipation of heat, thereby reducing the possibility of damage to the surrounding tissues. The example illustrated in FIG. 6 shows that the dissipation of heat is less rapid as compared to the rise in temperature due to induced current or other induced electrical activity.

In another embodiment, the size of the heat dissipation apparatus may spread the heat induced by an RF field over a relatively larger surface area than would be normally found at an electrode site. This larger surface area translates to lower temperature rise at any given point on the surface for a given amount of RF energy, by dissipating the same energy over a larger area.

Figure 7B:
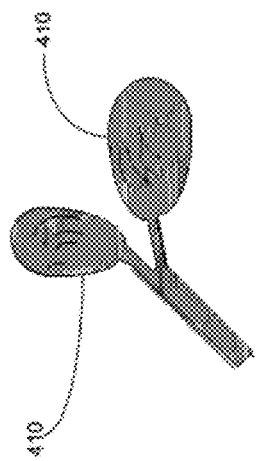
FIGS. 7A and 7B illustrate exemplary embodiments of a heat dissipation apparatus, in accordance with one illustrative embodiment of the present invention.

Turning now to FIGS. 7A, 7B, 8A and 8B, various shapes for implementing the heat dissipation apparatus 410, are illustrated. In the embodiment illustrated in FIG. 7A, an electrical/thermal connection to a flat, round or elliptical heat dissipation apparatus 410 may be provided. This shape may provide for efficient distribution of thermal energy at a predetermined rate based upon the type of conductor used and the type of electrical and/or thermal insulations 520, 510. As illustrated in FIG. 7B, one electrical/thermal connection may lead to two dissipation apparatuses 410. This may provide for more efficient dissipation of heat and provide capacity to direct substantial thermal energy away from portions of the electrode.

Figure 8B:
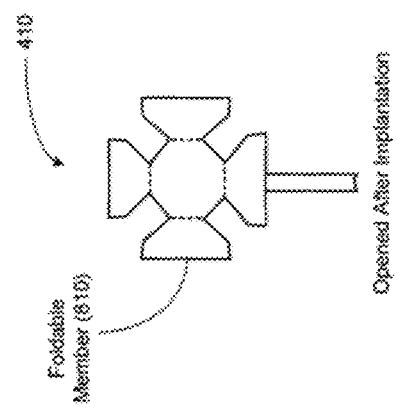
FIGS. 8A and 8B illustrate an exemplary heat dissipation apparatus that may be retractable and extractable, in accordance with one illustrative embodiment of the present invention.
Figure 7A:
Figure 8A:
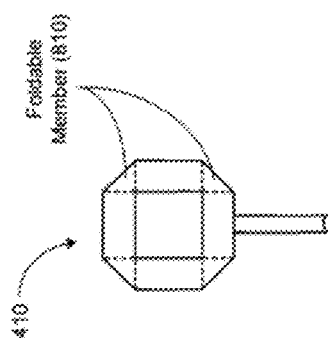

Further, as illustrated in FIG. 8A, a heat dissipation apparatus 410 may comprise various foldable members (e.g., foldable wings) 810. The foldable members 810 may be folded or retracted while the electrode is inserted into the human body. As illustrated in FIG. 8B, once implanted, the foldable members 810 may be expanded outward to provide a greater area for heat dissipation. The opening, or the expanding of the foldable members 810 of the heat dissipation apparatus 410 of FIGS. 8A and 8B, may be prompted by various stimuli. For example, a mechanical manipulation of the lead/electrode may be provided to cause the foldable wings 810 of the heat dissipation apparatus 410 of FIGS. 8A and 8B to expand. Other techniques such as an electrical indication may be provided to prompt the expansion or contraction of the foldable wings 810 of the heat dissipation apparatus. The expansion of the length of the heat dissipation apparatus 410 of FIGS. 8A and 8B may also be prompted by a predetermined temperature range. For example, the heat dissipation apparatus 410 of FIGS. 8A and 8B may be formed such that exposure to a particular temperature range (e.g., normal human body temperature range, externally provided heat, etc), may cause the foldable members 810 to expand, thereby providing greater area for dissipation of thermal energy.

Figure 9:
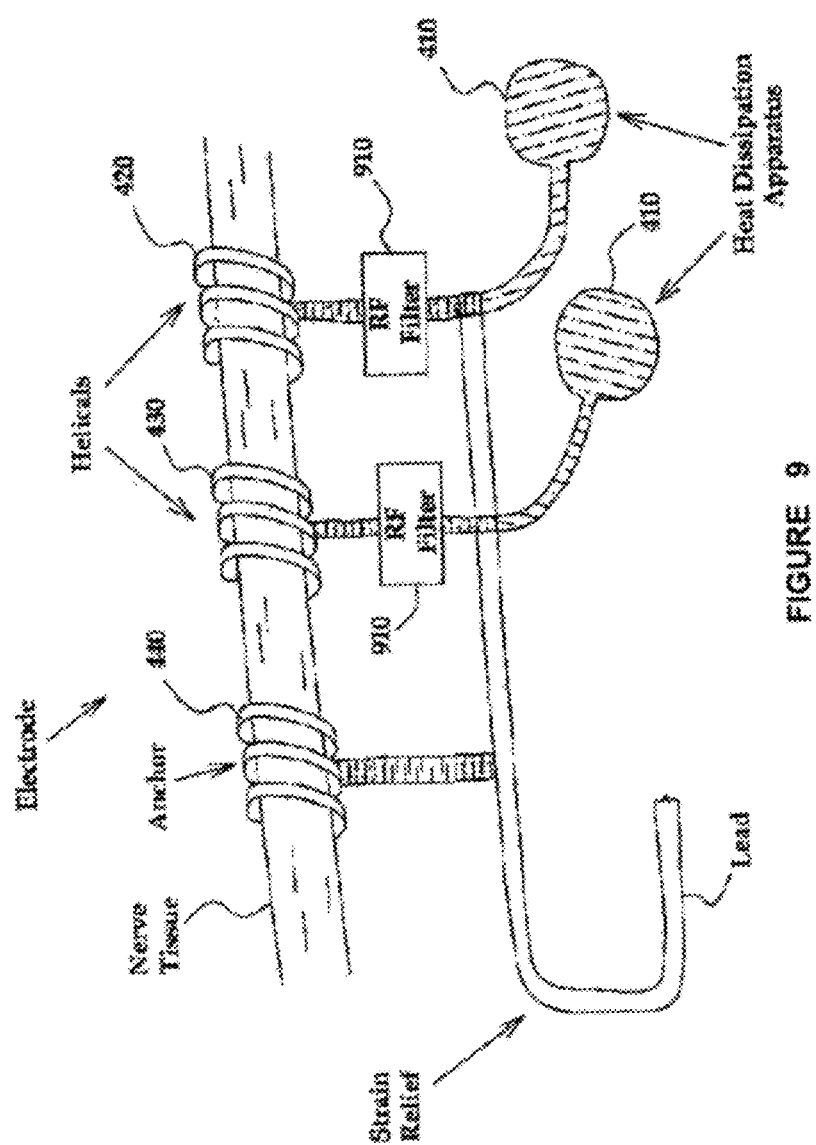
FIG. 9 illustrates an electrode/lead assembly that includes a heat dissipation apparatus and one or more RF filters, in accordance with one illustrative embodiment of the present invention.

Turning now to FIG. 9, an alternative embodiment of the electrode/lead assembly, in accordance with one illustrative embodiment of the present invention, is provided. As illustrated in FIG. 9, the electrode may comprise a first and second helical structure 420, 430 to provide a positive and negative node for electrical signals. In one embodiment, an RF filter 910, may be implemented into the electrode/lead assembly. The RF filter 910 may provide for filtering various induced current from traveling to certain portions of the electrode/lead assembly. In one embodiment, the RF filters may be positioned proximate to the first and second helicals 420, 430. Hence, RF induced current may be filtered from entering this region, thereby preventing or reducing the amount of thermal energy that may be induced by an RF induced current from coming into contact with more sensitive portions of the electrode (e.g., the helicals 430, 520). At the same time, the RF induced current may be allowed to flow to the heat dissipation apparatus 410, which is capable of dissipating the thermal energy caused by the induced current.

An RF filter 910 may also be positioned proximate to the anchor 440. Therefore, utilizing the embodiment of FIG. 9, the induced current traveling to the nerve tissue may be attenuated, all the while directing the induced current towards the heat dissipation apparatus 410. In this manner, the heat dissipation apparatus 410 is capable of more effectively dissipating the thermal energy caused by the induced current. Therefore, the tips of the electrode portions, such as the tips of helicals 420, 430 and/or the anchor 440, may experience a reduced amount of RF induced thermal energy. Therefore, damage to the nerve tissue may be reduced while more effectively dispersing thermal energy into other portions of the human body using the heat dissipation apparatus 410.

Figure 10:
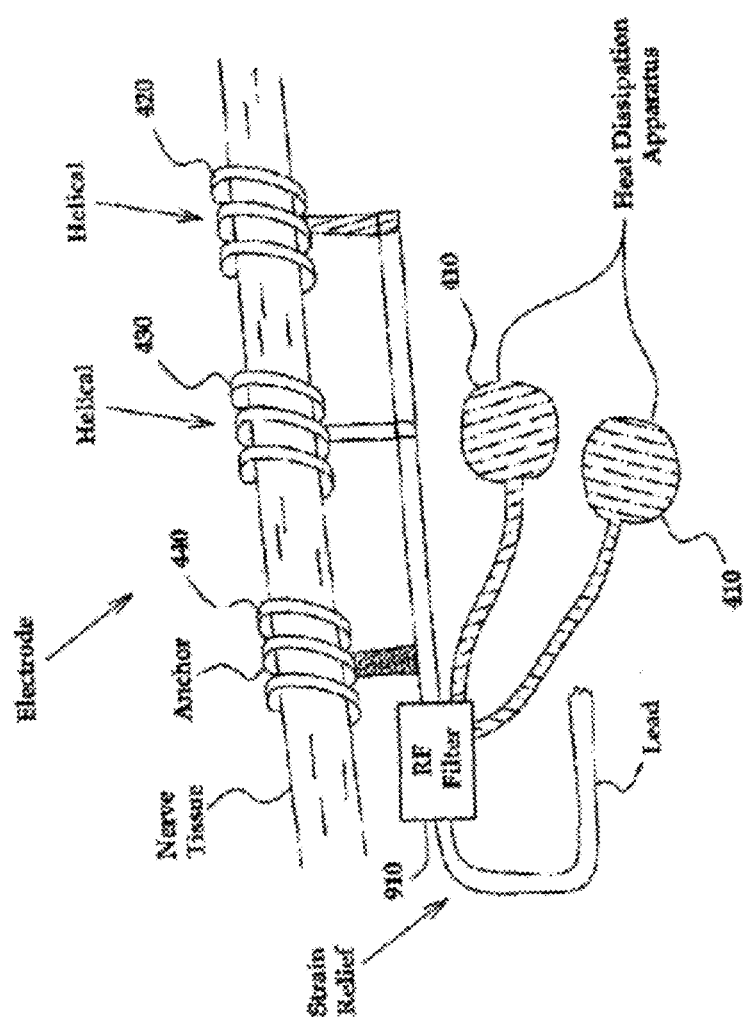
FIG. 10 illustrates an electrode/lead assembly that includes a heat dissipation apparatus, and an RF filter, in accordance with another illustrative embodiment of the present invention.

Turning now to FIG. 10, yet another alternative embodiment of implementing the heat dissipation apparatus 410, in accordance with one illustrative embodiment of the present invention, is provided. In one embodiment, the RF filter 910 may be positioned prior to the connection to the various portions of the electrode (i.e., the first and second helicals 420, 430 and the anchor 440). The RF filter 910 is capable of blocking significant amounts of RF induced current. The RF filter 910 may comprise circuitry that may provide for directing the induced currents towards the heat dissipation apparatus while preventing significant amount of induced current to flow towards portions of the electrode. The position of the RF filter 910 may be such that a maximum distance is maintained to prevent significant amount of induced current to be induced after the RF filter 910. In one embodiment, the neurostimulation nodes (the $1^{st}$ and $2^{nd}$ helicals 420, 430) of the electrode may be positioned equal to or less than 5 centimeters from the RF filter 910 for desirable interaction with the RF fields of up to about 128 MHz signals. Those skilled in the art having benefit of the present invention, would appreciate that various positioning of the RF filter 910 may be implemented to provide the benefits of directing induced currents more towards the heat dissipation apparatus 410 and away from the various neurostimulation delivery portions of the electrode, and remain within the spirit and scope of the present invention.

Turning now to FIG. 11, a capacitive coupling arrangement of the electrode/lead assembly provided by an illustrative embodiment of the present invention is depicted. The heat dissipation apparatuses 410, in FIG. 11, may be arranged in such a manner that a capacitive coupling effect may be realized. In one embodiment, the heat dissipation apparatuses 410 may be positioned with an electrical insulator 1110 in between. Effectively, this configuration is essentially two conductors with a dielectric in between, which provides for a capacitive coupling by the heat dissipation apparatuses 410. Using the capacitive coupling configuration of FIG. 11, a high frequency energy shunt path may be generated. This shunt path for high frequency energy may provide for directing energy away from the nerve tissue upon which the various portions of electrodes are coupled. Therefore, thermal energy may be directed away from the nerve tissue due to the capacitive coupling effect of the heat dissipation apparatus provided by the configuration of FIG. 11.

Turning now to FIG. 12, an alternative "veined" structure for providing the heat dissipation, in accordance with an alternative illustrative embodiment of the present invention, is provided. In one embodiment, the veined structure may be in a first configuration 1210 that provides for a plurality of branched collection of wires that may be folded back within the space of the heat dissipation apparatus 410 illustrated in FIG. 4. Each of the wires associated with the branch of wires 1210 may be formed to respond to a particular frequency to be targeted for dissipation of induced current. In one embodiment, each of the individual wires in the brand of wires 1210 may be of different predetermined length, wherein each wire may be tuned to a predetermined frequency. Therefore, each wire may be tuned to respond to a particular induced current. The group of wires may form a veined structure 1210 to provide heat dissipation and to direct thermal energy away from the nerve tissue. The group of wires that form the vein structure 1220 may provide for a plurality of wires that are tuned to particular frequencies that are grouped in a spiraled manner. The spiral veined configuration 1220 may provide for responding to pre-determined frequencies. The group of wires that form the spiral structure 1210 may also provide heat dissipation and direct thermal energy away from the nerve tissue.

Utilizing embodiments of the present invention, thermal energy that could have occurred at the various portions of an electrode, such as the tips of the various nodes may be reduced by more efficiently and effectively dispersing thermal energy in a less hostile manner into the patient's body. The electrode lead assembly provided by embodiments of the present invention may be adapted to a variety of types of implantable medical devices and still remain within the spirit and scope of the present invention.

All of the methods and apparatus disclosed and claimed herein may be made and executed without undue experimentation in light of the present disclosure. While the methods and apparatus of this invention have been described in terms of particular embodiments, it will be apparent to those skilled in the art that variations may be applied to the methods and apparatus and in the steps or in the sequence of steps of the method described herein without departing from the concept, spirit, and scope of the invention, as defined by the appended claims. It should be especially apparent that the principles of the invention may be applied to selected cranial nerves other than the vagus nerve to achieve particular results.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed:

1. An electrode system for delivering an electrical signal to a first tissue of a patient's body, said electrode system comprising:
    a lead; and
    an electrode coupled to said lead, comprising
        a stimulation portion adapted to be coupled to said first tissue and adapted to deliver an electrical signal to said first tissue;
        a dissipation portion that is not adapted to interface with said first tissue, wherein said dissipation portion is branching off the lead along a distal branch, wherein said dissipation portion is adapted to interface with a second tissue, said dissipation portion capable of dissipating thermal energy by receiving at least a portion of an induced current on the lead; and
        an insulator surrounding at least a portion of said dissipation portion, wherein said insulator is a thermal insulator for at least partially attenuating dissipation of said thermal energy, wherein said insulator further comprises an electrical insulator.

2. The electrode system of claim 1, wherein said stimulation portion comprises an electrode pair comprising a cathode and an anode for selectively receiving a neurostimulation signal applied to said electrode.

3. The electrode system of claim 1, wherein said dissipation portion comprises a conductive disc for distributing said thermal energy.

4. The electrode system of claim 1, wherein the electrode comprises a plurality of dissipation portions, and wherein each said dissipation portion is not adapted to interface with said first tissue.

5. The electrode system of claim 4, wherein said plurality of dissipation portions are disposed in close physical proximity to one another to thereby form a capacitive coupling of the conductors of said dissipation portions, to provide a shunt path for directing thermal energy away from said first tissue.

6. The electrode system of claim 1, wherein said dissipation portion of said electrode comprises a plurality of wires of a predetermined size to direct electrical energy away from said first tissue.

7. The electrode system of claim 6, wherein said plurality of wires are formed into a folded bundle, each of said wires being responsive to a predetermined frequency of a radio frequency (RF) energy.

8. The electrode system of claim 6, wherein said plurality of wires are formed into a spiral bundle, each of said wires being responsive to a predetermined frequency of a radio frequency (RF) energy.

9. The electrode system of claim 1, wherein said dissipation portion comprises at least one collapsible member capable of expanding in response to at least one of a mechanical stimulation, an electrical stimulation, and a thermal stimulation.

10. The electrode system of claim 1, wherein said dissipation portion is capable of dissipating thermal energy resulting from a current induced by at least one of an electrical field, a magnetic field, and an electromagnetic field.

11. The electrode system of claim 1, further comprising a filter unit adapted to substantially attenuate a current induced on the lead by a radio frequency (RF) signal.

12. The electrode system of claim 1, wherein said stimulation portion is not an end portion of said electrode.

13. A neurostimulation lead assembly for providing a neurostimulation signal to a portion of a first tissue of a patient's body, comprising:
- a lead for conducting a neurostimulation signal; and
- an electrode operatively coupled to said lead, said electrode comprising:
  - an electrical signal delivery portion adapted to be coupled to said first tissue to deliver said neurostimulation signal to said first tissue; and
  - a heat dissipation portion that is not interfaced with said first tissue, wherein said heat dissipation portion is branching off the lead along a branch, wherein said heat dissipation portion is adapted to interface with a second tissue, said heat dissipation portion capable of dissipating thermal energy by receiving at least a portion of an induced current on the lead, said heat dissipation portion further comprising an insulator surrounding at least a portion of said heat dissipation portion.

14. The neurostimulation lead assembly of claim 13, further comprising a filter unit adapted to substantially attenuate a current induced on the lead by at least one of an electrical field, a magnetic field, and an electromagnetic field.

15. An implantable medical device system to provide an electrical signal to a portion of a patient's body to treat a disorder, comprising:
- an implantable medical device for generating an electrical signal;
- a lead; and
- an electrode operatively coupled to said implantable medical device and to said lead for delivering said electrical signal to a first tissue of a patient's body, said electrode comprising:
  - an electrical signal delivery portion adapted to be coupled to said first tissue to deliver said electrical signal to said first tissue; and
  - a heat dissipation portion that does not interface with said first tissue, wherein said heat dissipation portion is branching off the lead along a branch, wherein said heat dissipation portion is adapted to interface with a second tissue, said heat dissipation portion capable of dissipating thermal energy by receiving at least a portion of an induced current on the lead, said heat dissipation portion further comprising an insulator substantially surrounding at least a portion of said heat dissipation portion.

16. The implantable medical device system of claim 15, wherein said insulator is at least one of a thermal insulator and an electrical insulator for at least one of attenuating dissipation of said thermal energy and insulating the tissue from an effect of said induced current.

17. The implantable medical device system of claim 15, wherein said heat dissipation portion of said electrode comprises a conductive disc for distributing said thermal energy.

18. The implantable medical device system of claim 15, wherein said heat dissipation portion of said electrode comprises a veined structure comprising a plurality of wires, wherein at least one of the length and the shape of each said wire is adapted to reduce induced heating of said first tissue for predetermined frequencies of a radio frequency (RF) signal coupled to said electrode.

19. The implantable medical device system of claim 15, wherein said heat dissipation portion is capable of dissipating thermal energy resulting from a current induced by at least one of an electrical field, a magnetic field, and an electromagnetic field.

20. The implantable medical device system of claim 15, wherein said electrical signal delivery portion comprises a first helical portion to provide a cathode and a second helical portion to provide an anode, and an anchor portion adapted to affix said electrical signal delivery portion to said nerve tissue; and
- said heat dissipation portion comprises at least one heat dissipation element to dissipate said thermal energy from said electrode.

21. An electrode system for delivering an electrical signal to a first tissue of a patient's body, comprising:
- a lead; and
- an electrode coupled to said lead, said electrode comprising
  - a stimulation portion adapted to be coupled to said first tissue to deliver an electrical signal to said first tissue, said stimulation portion not being an end portion of said electrode; and
  - a dissipation portion that interfaces with a second tissue, wherein said dissipation portion is branching off the lead along a branch, said dissipation portion capable of dissipating thermal energy by receiving at least a portion of an induced current on the lead, wherein said dissipation portion comprises a conductive disc for distributing said thermal energy, wherein said dissipation portion further comprising an insulator surrounding at least a portion of said dissipation portion.

22. The electrode system of claim 21, wherein said electrode further comprises a sensing portion that couples to said first tissue to sense a physiological indication.

* * * * *